(12) United States Patent
Helm et al.

(10) Patent No.: US 11,969,279 B2
(45) Date of Patent: *Apr. 30, 2024

(54) METHOD AND APPARATUS FOR RECONSTRUCTING IMAGE PROJECTIONS

(71) Applicant: Medtronic Navigation, Inc., Louisville, CO (US)

(72) Inventors: Patrick A. Helm, Milton, MA (US); Shuanghe Shi, Southborough, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 308 days.

This patent is subject to a terminal disclaimer.

(21) Appl. No.: 15/823,031

(22) Filed: Nov. 27, 2017

(65) Prior Publication Data

US 2018/0078226 A1    Mar. 22, 2018

Related U.S. Application Data

(63) Continuation of application No. 13/016,718, filed on Jan. 28, 2011, now abandoned, which is a
(Continued)

(51) Int. Cl.
*A61B 6/00* (2006.01)
*A61B 6/02* (2006.01)
(Continued)

(52) U.S. Cl.
CPC ............... *A61B 6/481* (2013.01); *A61B 6/02* (2013.01); *A61B 6/4405* (2013.01);
(Continued)

(58) Field of Classification Search
CPC .......... A61B 6/481; A61B 6/482; A61B 6/032; A61B 6/504; A61B 5/7289; G06T 11/006;
(Continued)

(56) References Cited

U.S. PATENT DOCUMENTS 4,477,923 A    10/1984    Baumann et al.
4,611,340 A     9/1986    Okazaki
(Continued)

FOREIGN PATENT DOCUMENTS

CN    101049244 A    10/2007
EP    0486717 A1     5/1992
(Continued)

OTHER PUBLICATIONS

European Office Action dated Jan. 29, 2018 in corresponding/related European Application No. 11777009.9.
(Continued)

*Primary Examiner* — Vincent Rudolph
*Assistant Examiner* — Raphael Schwartz
(74) *Attorney, Agent, or Firm* — Harness, Dickey & Pierce, P.L.C.

(57) ABSTRACT

A method and system is disclosed for acquiring image data of a subject. The image data can be collected with an imaging system having a detector able to move relative to the subject. A contrast agent can be injected into the subject and image data can be acquired with the contrast agent in various phases of the subject. A volumetric model of multiple phases can be reconstructed selected reconstruction techniques.

20 Claims, 6 Drawing Sheets

Related U.S. Application Data continuation-in-part of application No. 12/908,189, filed on Oct. 20, 2010, now Pat. No. 9,807,860.

(51) Int. Cl.
| | |
|---|---|
| *A61B 6/46* | (2024.01) |
| *A61B 6/50* | (2024.01) |
| *A61B 34/20* | (2016.01) |
| *A61M 5/00* | (2006.01) |
| *G06T 11/00* | (2006.01) |
| *A61B 6/40* | (2024.01) |

(52) U.S. Cl.
CPC ............ *A61B 6/4476* (2013.01); *A61B 6/469* (2013.01); *A61B 6/482* (2013.01); *A61B 6/486* (2013.01); *A61B 6/503* (2013.01); *A61B 6/504* (2013.01); *A61B 6/507* (2013.01); *A61B 6/5288* (2013.01); *A61B 6/545* (2013.01); *A61M 5/007* (2013.01); *G06T 11/005* (2013.01); *A61B 6/4085* (2013.01); *A61B 34/20* (2016.02); *A61B 2576/023* (2013.01); *G01N 2223/419* (2013.01); *G06T 2207/10081* (2013.01); *G06T 2207/30048* (2013.01); *G06T 2211/404* (2013.01); *G06T 2211/412* (2013.01)

(58) Field of Classification Search
CPC .... G06T 2211/424; H05G 1/58; A61M 5/007; A61M 5/142
See application file for complete search history.

(56) References Cited

U.S. PATENT DOCUMENTS

| | | | |
|---|---|---|---|
| 4,672,651 A | 6/1987 | Horiba et al. | |
| 5,019,686 A | 5/1991 | Marantz | |
| 5,583,902 A | 12/1996 | Bae | |
| 5,689,629 A | 11/1997 | Lee | |
| 6,397,098 B1 | 5/2002 | Uber, III et al. | |
| 6,697,508 B2 | 2/2004 | Nelson | |
| 6,922,462 B2 | 7/2005 | Acharya et al. | |
| 7,386,089 B2 | 6/2008 | Endo et al. | |
| 7,460,635 B2 | 12/2008 | Fujimoto et al. | |
| 7,684,537 B2 | 3/2010 | Imai et al. | |
| 7,852,986 B2 | 12/2010 | Loef et al. | |
| 7,860,288 B2 | 12/2010 | Bernhardt et al. | |
| 8,107,709 B2 | 1/2012 | Kawamura et al. | |
| 9,769,912 B2 | 9/2017 | Helm et al. | |
| 9,807,860 B2 | 10/2017 | Helm et al. | |
| 2003/0050750 A1 | 3/2003 | Kosling et al. | |
| 2003/0152519 A1 | 8/2003 | Koenig et al. | |
| 2003/0161435 A1 | 8/2003 | Ozaki | |
| 2004/0101086 A1 | 5/2004 | Sabol et al. | |
| 2004/0101088 A1 | 5/2004 | Sabol et al. | |
| 2004/0116804 A1 | 6/2004 | Mostafavi | |
| 2004/0170254 A1 | 9/2004 | Gregerson et al. | |
| 2005/0080327 A1 | 4/2005 | Jenkins et al. | |
| 2005/0084060 A1 | 4/2005 | Seppi et al. | |
| 2005/0171426 A1 | 8/2005 | Rasche | |
| 2005/0201509 A1 | 9/2005 | Mostafavi et al. | |
| 2006/0052690 A1 | 3/2006 | Sirohey et al. | |
| 2006/0251216 A1 | 11/2006 | Allred et al. | |
| 2007/0009081 A1 | 1/2007 | Zhou et al. | |
| 2007/0055148 A1 | 3/2007 | Klingenbeck-Regn | |
| 2007/0167738 A1 | 7/2007 | Timinger et al. | |
| 2007/0238968 A1 | 10/2007 | Rappoport et al. | |
| 2008/0123928 A1 | 5/2008 | Harer et al. | |
| 2008/0206150 A1 | 8/2008 | Louie et al. | |
| 2008/0212743 A1 | 9/2008 | Gregerson et al. | |
| 2008/0232548 A1 | 9/2008 | Tanaka | |
| 2008/0240355 A1 | 10/2008 | Ohishi | |
| 2008/0242978 A1* | 10/2008 | Simon .................. A61B 90/36 |
| | | | 600/426 |
| 2008/0285722 A1* | 11/2008 | Bertolina ............. A61B 6/4411 |
| | | | 378/197 |
| 2008/0306381 A1 | 12/2008 | Feuerlein et al. | |
| 2009/0010380 A1 | 1/2009 | Gotoh | |
| 2009/0156927 A1 | 6/2009 | Schmidt | |
| 2009/0232374 A1 | 9/2009 | Simon | |
| 2010/0046817 A1 | 2/2010 | Goedicke et al. | |
| 2010/0114064 A1 | 5/2010 | Kalafut et al. | |
| 2010/0128942 A1* | 5/2010 | Licato .................. G06T 7/0014 |
| | | | 382/128 |
| 2010/0160776 A1 | 6/2010 | Goto et al. | |
| 2010/0183117 A1 | 7/2010 | Tsumuraya et al. | |
| 2010/0189210 A1 | 7/2010 | Nemoto | |
| 2010/0202585 A1 | 8/2010 | Zaiki | |
| 2010/0290690 A1 | 11/2010 | Hartmann et al. | |
| 2010/0292570 A1 | 11/2010 | Tsukagoshi | |
| 2011/0103542 A1 | 5/2011 | Allmendinger et al. | |
| 2011/0135177 A1 | 6/2011 | Ohishi | |
| 2012/0097178 A1 | 4/2012 | Helm et al. | |
| 2012/0099768 A1 | 4/2012 | Helm et al. | |
| 2012/0099772 A1 | 4/2012 | Helm et al. | |
| 2018/0007769 A1 | 1/2018 | Helm et al. | |
| 2018/0054880 A1 | 2/2018 | Helm et al. | |
| 2018/0078226 A1 | 3/2018 | Helm et al. | |

FOREIGN PATENT DOCUMENTS

| | | |
|---|---|---|
| EP | 1920717 A2 | 5/2008 |
| EP | 1980207 A1 | 10/2008 |
| JP | S59129053 A | 7/1984 |
| JP | 2000506398 A | 5/2000 |
| JP | 2001145619 A | 5/2001 |
| JP | 2003290192 A | 10/2003 |
| JP | 2004065975 A | 3/2004 |
| JP | 2005130929 A | 5/2005 |
| JP | 2005524419 A | 8/2005 |
| JP | 2005-270201 A | 10/2005 |
| JP | 2005-536288 A | 12/2005 |
| JP | 2006296707 A | 11/2006 |
| JP | 2007021184 A | 2/2007 |
| JP | 2007503905 A | 3/2007 |
| JP | 2007143880 A | 6/2007 |
| JP | 2007519443 A | 7/2007 |
| JP | 2007-195978 A | 8/2007 |
| JP | 2007319690 A | 12/2007 |
| JP | 2008062035 A | 3/2008 |
| JP | 2008073115 A | 4/2008 |
| JP | 2008096088 A | 4/2008 |
| JP | 2008518688 A | 6/2008 |
| JP | 2008-148886 A | 7/2008 |
| JP | 2008154718 A | 7/2008 |
| JP | 2008154811 A | 7/2008 |
| JP | 2008253758 A | 10/2008 |
| JP | 2008264273 A | 11/2008 |
| JP | 2009056795 A | 3/2009 |
| JP | 2009077839 A | 4/2009 |
| JP | 2009119111 A | 6/2009 |
| JP | 2009131632 A | 6/2009 |
| JP | 2009261519 A | 11/2009 |
| JP | 2009-297584 A | 12/2009 |
| JP | 2009279289 A | 12/2009 |
| JP | 2009297517 A | 12/2009 |
| JP | 2010503145 A | 1/2010 |
| JP | 2010081977 A | 4/2010 |
| JP | 2010-516401 A | 5/2010 |
| JP | 2010142478 A | 7/2010 |
| JP | 2010167254 A | 8/2010 |
| WO | 2005076810 A2 | 8/2005 |
| WO | 2006034984 A1 | 4/2006 |
| WO | 2009-020136 A1 | 2/2009 |
| WO | 2009083866 A1 | 7/2009 |
| WO | 2009123256 A1 | 10/2009 |
| WO | 2010015953 A2 | 2/2010 |
| WO | 2012054733 A2 | 4/2012 |

(56) References Cited

FOREIGN PATENT DOCUMENTS

| WO | 2012054740 A1 | 4/2012 |
|---|---|---|
| WO | 2012103302 A2 | 8/2012 |

OTHER PUBLICATIONS

"Medtronic O-Arm Multi-Dimensional Surgical Imaging System"; Brochure, 24pp, 2009.
Chinese Office Action dated Jun. 17, 2015 for China Patent Document No. 201180061207.4.
Chinese Office Action dated May 6, 2015 for China Patent Document No. 201180061219.7.
Chinese Office Action dated Nov. 2, 2014 for China Patent Document No. 201180061207.4.
European Office Action dated Mar. 10, 2016 for European Patent Application No. 11779032.9-1666.
European Office Action dated Sep. 22, 2015 for European Patent Application No. 11777009.9.
European Summons to Attend Oral Proceedings mailed Mar. 6, 2017 for European Patent Application No. 11777009.9 claiming benefit of PCT/US2011/057112 claiming benefit of U.S. Appl. No. 13/016,718, filed Jan. 28, 2011 and U.S. Appl. No. 12/908,189, filed Oct. 20, 2010.
Gordon, et al, Algebraic Reconstruction Techniques (ART) for Three-dimensional Electron Microscopy and X-ray Photography, Dec. 1970, vol. 29, Issue 3, pp. 471-476.
International Preliminary Report on Patentability and Written Opinion dated Aug. 8, 2013 for PCT/US2012/022673 claiming benefit of U.S. Appl. No. 13/016,718, filed Jan. 28, 2011.
International Preliminary Report on Patentability and Written Opinion dated May 2, 2013 for PCT/US2011/057121 claiming benefit of U.S. Appl. No. 12/908,200, filed Oct. 20, 2010.
International Search Report and Written Opinion dated Mar. 23, 2012 for PCT/US2011/057121 claiming benefit of U.S. Appl. No. 12/908,200, filed Oct. 20, 2010.
International Search Report dated Jul. 20, 2012 for PCT/US2012/022673 claiming benefit of U.S. Appl. No. 13/016,718, filed Jan. 28, 2011.
International Search Report dated July 3. 2012 for PCT/US2011/057112, claiming benefit of U.S. Appl. No. 12/908,189, filed Oct. 20, 2010 and U.S. Appl. No. 12/908,189, filed Oct. 20, 2010.
Invitation to Pay Additional Fees and Partial International Search dated Feb. 23, 2012 for PCT/US2011/057112 claiming benefit of U.S. Appl. No. 13/016,718, filed Jan. 28, 2011; and U.S. Appl. No. 12/908,189, filed Oct. 20, 2010.
Invitation to Pay Additional Fees and Partial International Search dated Feb. 7, 2012 for PCT/US2011/057121 claiming benefit of U.S. Appl. No. 12/908,200, filed Oct. 20, 2010.
Japanese Office Action dated Aug. 9, 2016 for Japanese Application No. 2015-017400 for PCT/US2011/057112 which claims benefit of U.S. Appl. No. 13/016,718, filed Jan. 28, 2011 with English translation.
Japanese Office Action dated Mar. 11, 2014 for Japanese Application No. JP2013-535094 filed Apr. 19, 2013, claiming benefit of U.S. Appl. No. 12/908,200, filed Oct. 20, 2010.
Japanese Office Action dated Mar. 25, 2014 for Japanese Application No. JP2013-535091 filed Apr. 19, 2013, claiming benefit of U.S. Appl. No. 12/908,189, filed Oct. 20, 2010 and U.S. Appl. No. 13/016,718, filed Jan. 28, 2011.
Japanese Office Action dated Nov. 4, 2014 for Japan Patent Document No. 2013-535094.
Japanese Office Action dated Sep. 12, 2017 in corresponding Japanese Application No. 2016-239270.
Johnson, Thorsten RC, et al. "Material differentiation by dual energy CT: Initial experience." European radiology 17.6 (2007); 1510-1517.
Li "Dual-Energy CT with Fast-kVp Switching and Its Applications in Orthopedics" OMICS J Radiology, vol. 2, Issue 6, 8 pages, 2013.
Montagnat, J. et al., "Globally constrained deformable models for 3D object reconstruction," Signal Processing 71.2: 173-186 (1998).
Japanese Office Action dated May 15, 2018 in corresponding/related Japanese Application No. 2016-239270.
European Office Action dated Jul. 25, 2018 in corresponding/related European Application No. 18171106.0.
Japanese Office Action dated Sep. 3, 2019 in corresponding/related Japanese Application No. 2018-174178.
Office Action dated Mar. 31, 2020 in corresponding/related Japanese Application No. 2018-174178.
Johnson, Thorsten RC, etal. "Material differentiation by dual energy CT: initial experience." European radiology 17.6 (2007): 1510-1517. (Year: 2007).
Office Action dated Jun. 24, 2020 in corresponding/related European Application No. 18171106.0.
Office Action regarding Japanese Patent Application No. 2020-124405, dated Dec. 7, 2021.
Japanese Office Action (with English Translation) for corresponding Application No. 201680073548.6 dated Apr. 6, 2021.
Extended European Search Report regarding EP 20184855.3, dated Apr. 20, 2021.
Matsumoto, Masato, et al. "3D-CT arteriography and 3D-CT venography: the separate demonstration of arterial-phase and venous-phase on 3D-CT angiography in a single procedure." American journal of neuroradiology 26.3 (2005): 635-641. (Year: 2005).
European Office Action dated Oct. 19, 2023, for realted European Patent Application No. 20184855.3, 5 pages.
U.S. Appl. No. 12/908,189, now U.S. Pat. No. 9,807,860, filed Oct. 20, 2010, Helm et al.
U.S. Appl. No. 13/016,718, 2012/0099768, filed Jan. 28, 2011, Helm et al.
U.S. Appl. No. 12/908,200, now U.S. Pat. No. 9,769,912, filed Oct. 20, 2010, Helm et al.
U.S. Appl. No. 15/797,429, 2018/0054880, filed Oct. 30, 2017, Helm et al.
U.S. Appl. No. 15/707,387, 2018/0007769, filed Sep. 18, 2017, Helm et al.

\* cited by examiner

METHOD AND APPARATUS FOR RECONSTRUCTING IMAGE PROJECTIONS

CROSS-REFERENCE TO RELATED APPLICATIONS

This application is a continuation of U.S. patent application Ser. No. 13/016,718 filed on Jan. 28, 2011, which is a continuation-in-part of U.S. patent application Ser. No. 12/908,189 filed on Oct. 20, 2010, now U.S. Pat. No. 9,807,860. The entire disclosure of the above application is incorporated herein by reference.

FIELD

The present disclosure relates to imaging a subject, and particularly to determining and performing an optimal image data acquisition of the subject to model various physiological characteristic and anatomical features of the subject.

BACKGROUND

This section provides background information related to the present disclosure which is not necessarily prior art.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the subject with images of the patient that can be acquired using imaging systems such as a magnetic resonance imaging (MRI) system, computed tomography (CT) system, fluoroscopy (e.g. C-Arm imaging systems), or other appropriate imaging systems.

Images of a patient can assist a surgeon in performing a procedure including planning the procedure and performing the procedure. A surgeon may select a two dimensional image or a three dimensional image representation of the patient. The images can assist the surgeon in performing a procedure with a less invasive technique by allowing the surgeon to view the anatomy of the patient without removing the overlying tissue (including dermal and muscular tissue) when performing a procedure.

SUMMARY

This section provides a general summary of the disclosure, and is not a comprehensive disclosure of its full scope or all of its features.

According to various embodiments, a system to acquire image data of a patient with an imaging system using enhanced contrast imaging can include an imaging system having a first energy source with a first energy parameters and a second energy source with a second energy parameters. The imaging system can also include a pump operable to inject a contrast agent into the patient with an instruction. A controller can be in communication with both the imaging system and the pump. The imaging system can communicate with the pump through the controller regarding timing of the injection of a contrast agent into the patient and is further operable to acquire image data based upon the timing of the injection of the contrast agent and/or the clinical procedure.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
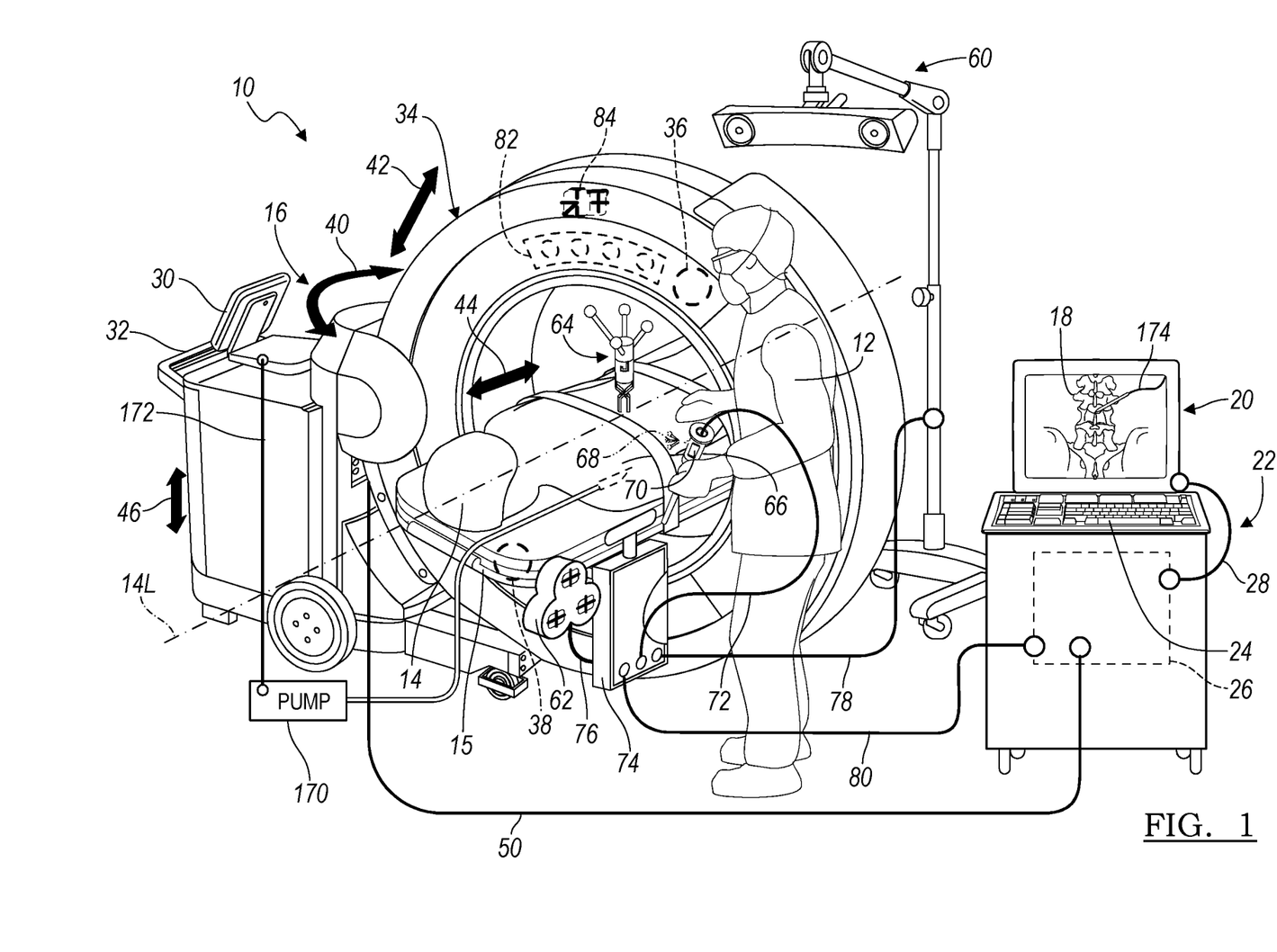
FIG. 1 is an environmental view of an imaging system in an operating theatre.

With reference to FIG. 1, in an operating theatre or operating room 10, a user, such as a surgeon 12, can perform a procedure on a patient 14. In performing the procedure, the user 12 can use an imaging system 16 to acquire image data of the patient 14 for performing a procedure. A model can be generated using the image data and displayed as image data 18 on a display device 20. The display device 20 can be part of a processor system 22 that includes an input device 24, such as a keyboard, and a processor 26 which can include one or more processors or microprocessors incorporated with the processing system 22. A connection 28 can be provided between the processor 26 and the display device 20 for data communication to allow driving the display device 20 to illustrate the image data 18.

The imaging system 16 can include an O-Arm® imaging system sold by Medtronic Navigation, Inc. having a place of business in Louisville, CO, USA. The imaging system 16, including the O-Arm® imaging system, or other appropriate imaging systems in use during a selected procedure are also described in U.S. patent application Ser. No. 12/465,206 filed on May 13, 2009, incorporated herein by reference.

The O-Arm® imaging system 16 includes a mobile cart 30 that includes a control panel or system 32 and an imaging gantry 34 in which is positioned a source unit 36 and a detector 38. The mobile cart 30 can be moved from one operating theater to another and the gantry 34 can move relative to the cart 30, as discussed further herein. This allows the imaging system 16 to be mobile thus allowing it to be used in multiple locations and with multiple procedures without requiring a capital expenditure or space dedicated to a fixed imaging system.

The source unit 36 can emit x-rays through the patient 14 to be detected by the detector 38. As is understood by one skilled in the art, the x-rays emitted by the source 36 can be emitted in a cone and detected by the detector 38. The source/detector unit 36/38 is generally diametrically opposed within the gantry 34. The detector 38 can move in a 360° motion around the patient 14 within the gantry 34 with the source 36 remaining generally 180° opposed to the detector 38. Also, the gantry 34 can move isometrically relative to the subject 14, which can be placed on a patient support or table 15, generally in the direction of arrow 40 as illustrated herein. The gantry 34 can also tilt relative to the patient 14 illustrated by arrows 42, move longitudinally along the line 44 relative to a longitudinal axis 14L of the patient 14 and the cart 30, can move up and down generally along the line 46 relative to the cart 30 and transversely to the patient 14, to allow for positioning of the source/detector 36/38 relative to the patient 14. The O-Arm® imaging device 16 can be precisely controlled to move the source/detector 36/38 relative to the patient 14 to generate precise image data of the patient 14. The imaging device 16 can be connected with the processor 26 via connection 50 which can include a wired or wireless connection or physical media transfer from the imaging system 16 to the processor 26. Thus, image data collected with the imaging system 16 can be transferred to the processing system 22 for navigation, display, reconstruction, etc.

Briefly, according to various embodiments, the imaging system 16 can be used with an unnavigated or navigated procedure. In a navigated procedure, a localizer, including either or both of an optical localizer 60 and an electromagnetic localizer 62 can be used to generate a field or receive or send a signal within a navigation domain relative to the patient 14. The navigated space or navigational domain relative to the patient 14 can be registered to the image data 18 to allow registration of a navigation space defined within the navigational domain and an image space defined by the image data 18. A patient tracker or dynamic reference frame 64 can be connected to the patient 14 to allow for a dynamic registration and maintenance of registration of the patient 14 to the image data 18.

A patient tracking device or dynamic registration device 64 and an instrument 66 can then be tracked relative to the patient 14 to allow for a navigated procedure. The instrument 66 can include an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation interface device 74 as can the electromagnetic localizer 62 with communication line 76 and/or the optical localizer 60 with communication line 78. Using the communication lines 74, 78 respectively, the probe interface 74 can then communicate with the processor 26 with a communication line 80. It will be understood that any of the communication lines 28, 50, 76, 78, or 80 can be wired, wireless, physical media transmission or movement, or any other appropriate communication. Nevertheless, the appropriate communication systems can be provided with the respective localizers to allow for tracking of the instrument 66 relative to the patient 14 to allow for illustration of the tracked location of the instrument 66 relative to the image data 18 for performing a procedure.

It will be understood that the instrument 66 being any appropriate instrument, such as a ventricular or vascular stent, spinal implant, neurological stent or stimulator, ablation device, or the like. The instrument 66 can be an interventional instrument or can include or be an implantable device. Tracking the instrument 66 allows for viewing the instrument's 66 location relative to the patient 14 with use of the registered image data 18 without direct viewing of the instrument 66 within the patient 14.

Further, the gantry 34 can include an optical tracking device 82 or an electromagnetic tracking device 84 to be tracked with a respective optical localizer 60 or electromagnetic localizer 62. Accordingly, the imaging device 16 can be tracked relative to the patient 14 as can the instrument 66 to allow for initial registration, automatic registration or continued registration of the patient 14 relative to the image data 18. Registration and navigated procedures are discussed in the above incorporated U.S. patent application Ser. No. 12/465,206.

Figure 2:
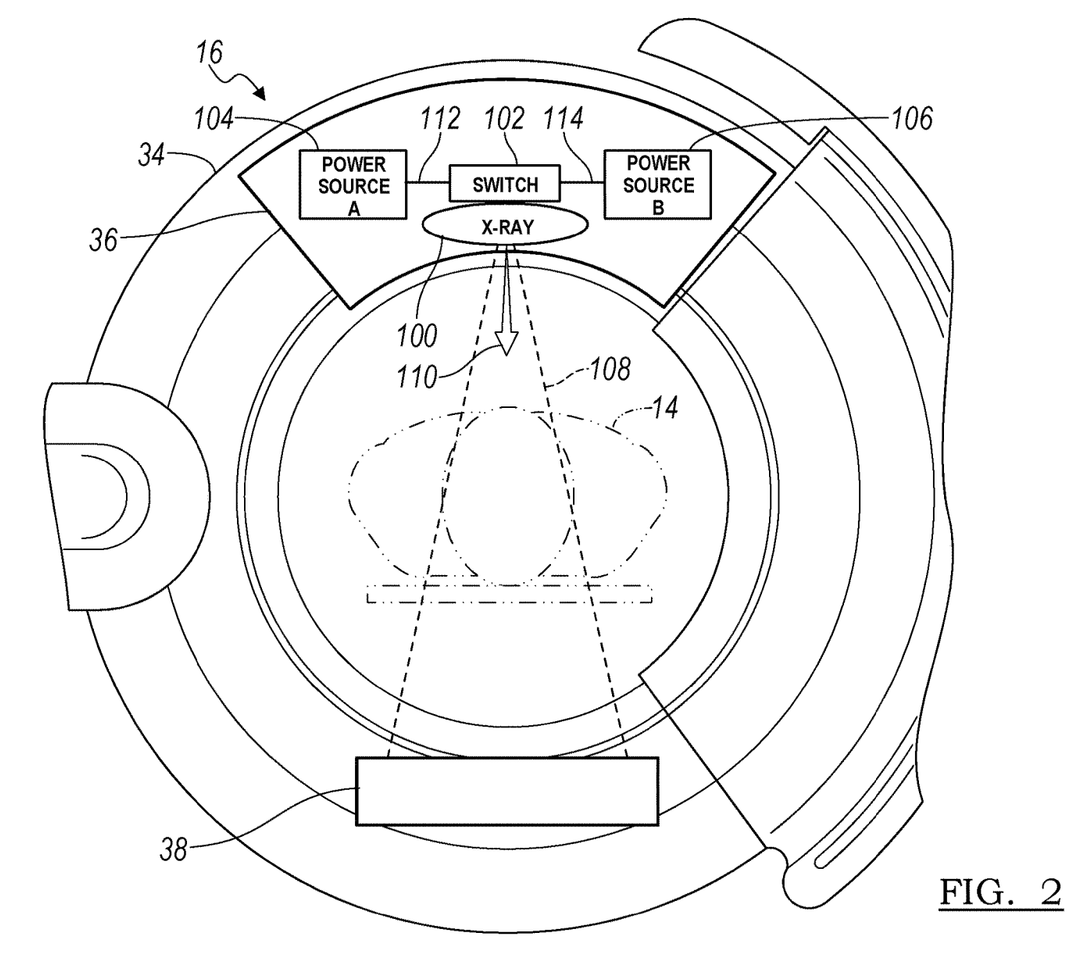
FIG. 2 is a detail view of an imaging system with a dual energy source system.

With reference to FIG. 2, according to various embodiments, the source 36 can include a single x-ray tube 100 that can be connected to a switch 102 that can interconnect a power source A 104 and a power source B 106 with the x-ray tube 100. X-rays can be emitted generally in a cone shape 108 towards the detector 38 and generally in the direction of the vector 110. The switch 102 can switch between the power source A 104 and the power source B 106 to power the x-ray tube 100 at different voltages and amperages to emit x-rays at different energies generally in the direction of the vector 110 towards the detector 38. It will be understood, however, that the switch 102 can also be connected to a single power source that is able to provide power at different voltages and amperages rather than the 102 switch that connects to two different power sources A 104, and B 106. Also, the switch 102 can be a switch that operates to switch a single power source between different voltages and amperages. The patient 14 can be positioned within the x-ray cone 108 to allow for acquiring image data of the patient 14 based upon the emission of x-rays in the direction of vector 110 towards the detector 38.

The two power sources A and B 104, 106 can be provided within the source housing 36 or can be separate from the source 36 and simply be connected with the switch 102 via appropriate electric connections such as a first cable or wire 112 and a second cable or wire 114. The switch 102 can switch between the power source A 104 and the power source B 106 at an appropriate rate to allow for emission of x-rays at two different energies through the patient 14 for various imaging procedures, as discussed further herein. The differing energies can be used for material separation and/or material enhanced reconstruction or imaging of the patient 14.

The switching rate of the switch 102 can include about 1 millisecond to about 1 second, further including about 10 ms to 500 ms, and further including about 50 ms. Further, the power source A 104 and the power source B 106 can include different power characteristics, including different voltages and different amperages, based upon selected contrast enhancement requirements. For example, as discussed further herein, it can be selected to allow for contrast enhancement between soft tissue (e.g. muscle or vasculature) and hard tissue (e.g. bone) in the patient 14 or between a contrast agent injected in the patient 14 and an area without a contrast agent injected in the patient 14.

As an example, the power source A 104 can have a voltage of about 75 kV and can have an amperage of about 50 mA, which can differ from the power source B which can have a voltage of 125 kV and 20 mA. The selected voltages and amperages can then be switched with the switch 102 to power the x-ray tube 100 to emit the appropriate x-rays generally in the direction of the vector 110 through the patient 14 to the detector 38. It will be understood that the range of voltages can be about 40 kV to about 140 kV (including about 40 kV to about 120 kV, and including about 50 kV to about 80 kV) and the amperages can be about 10 mA to about 500 mA. Generally, the power characteristics differences between the first power source A 104 and the second power source B 106 can be about 40 kV to about 60 kV and about 20 mA to about 150 mA.

The dual power sources allow for dual energy x-rays to be emitted by the x-ray tube 100. As discussed above, the two or dual energy x-rays can allow for enhanced and/or dynamic contrast reconstruction of models of the subject 14 based upon the image data acquired of the patient 14. Generally an iterative or algebraic process can be used to reconstruct the model of at least a portion of the patient 14 based upon the acquired image data. It will be understood, however, that any appropriate number of power sources or switching possibilities can be provided. Two is included in the subject disclosure merely for clarity of the current discussion.

The power sources can power the x-ray tube 100 to generate two dimension (2D) x-ray projections of the patient 14, selected portion of the patient 14, or any area, region or volume of interest. The 2D x-ray projections can be reconstructed, as discussed herein, to generate and/or display three-dimensional (3D) volumetric models of the patient 14, selected portion of the patient 14, or any area, region or volume of interest. As discussed herein, the 2D x-ray projections can be image data acquired with the imaging system 16, while the 3D volumetric models can be generated or model image data.

Appropriate algebraic techniques include Expectation maximization (EM), Ordered Subsets EM (OS-EM), Simultaneous Algebraic Reconstruction Technique (SART) and Total Variation Minimization (TVM), as generally understood by those skilled in the art. The application to performing a 3D volumetric reconstruction based on the 2D projections allows for efficient and complete volumetric reconstruction. Generally, an algebraic technique can include an iterative process to perform a reconstruction of the patient 14 for display as the image data 18. For example, a pure or theoretical image data projection, such as those based on or generated from an atlas or stylized model of a "theoretical" patient, can be iteratively changed until the theoretical projection images match the acquired 2D projection image data of the patient 14. Then, the stylized model can be appropriately altered as the 3D volumetric reconstruction model of the acquired 2D projection image data of the selected patient 14 and can be used in a surgical intervention, such as navigation, diagnosis, or planning. The theoretical model can be associated with theoretical image data to construct the theoretical model. In this way, the model or the image data 18 can be built based upon image data acquired of the patient 14 with the imaging device 16.

The 2D projection image data can be acquired by substantially annular or 360° orientation movement of the source/detector 36/38 around the patient 14 due to positioning of the source/detector 36/38 moving around the patient 14 in the optimal movement. Also, due to movements of the gantry 34, the detector need never move in a pure circle, but rather can move in a spiral helix, or other rotary movement about or relative to the patient 14. Also, the path can be substantially non-symmetrical and/or non-linear based on movements of the imaging system 16, including the gantry 34 and the detector 38 together. In other words, the path need not be continuous in that the detector 38 and the gantry 34 can stop, move back the direction from which it just came (e.g. oscillate), etc. in following the optimal path. Thus, the detector 38 need never travel a full 360° around the patient 14 as the gantry 34 may tilt or otherwise move and the detector 38 may stop and move back in the direction it has already passed.

In acquiring image data at the detector 38, the dual energy x-rays generally interact with a tissue and/or a contrast agent in the patient 14 differently based upon the characteristics of the tissue or the contrast agent in the patient 14 and the energies of the two x-rays emitted by the x-ray tube 100. For example, the soft tissue of the patient 14 can absorb or scatter x-rays having an energy produced by the power source A 104 differently than the x-rays having energy produced by the power source B 106. Similarly, a contrast agent, such as iodine, can absorb or scatter the x-rays generated by the power source A 104 differently from those generated by the power source B 106. Switching between the power source A 104 and the power source B 106 can allow for determination of different types of material properties (e.g. hard or soft anatomy), or contrast agent, implants, etc. within the patient 14. By switching between the two power sources 104, 106 and knowing the time when the power source A 104 is used to generate the x-rays as opposed to the power source B 106 to generate the x-rays the information detected at the detector 38 can be used to identify or segregate the different types of anatomy or contrast agent being imaged.

A timer can be used to determine the time when the first power source A 104 is being used and when the second power source B 106 is being used. This can allow the images to be indexed and separated for generating different models of the patient 14. Also, as discussed herein, the timer, which can be a separate system or included with the imaging system 16 or the processor system 26, can be used to index image data generated with the contrast agent injected into the patient 14.

Figure 3A:
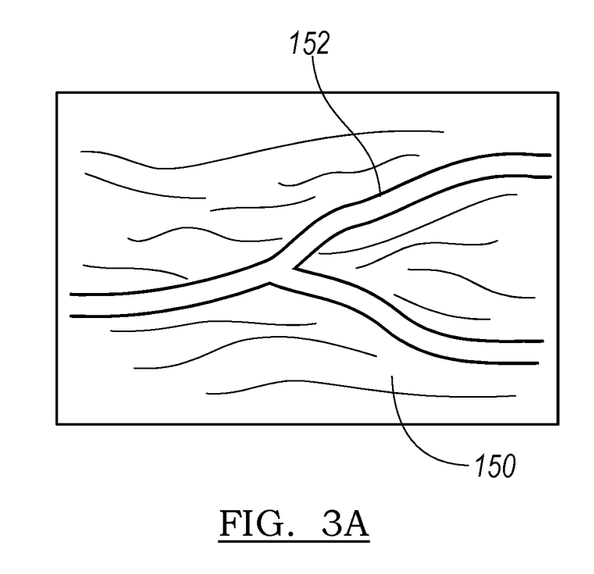
FIG. 3A is a schematic representation of non-contrast enhanced image data.
Figure 3B:
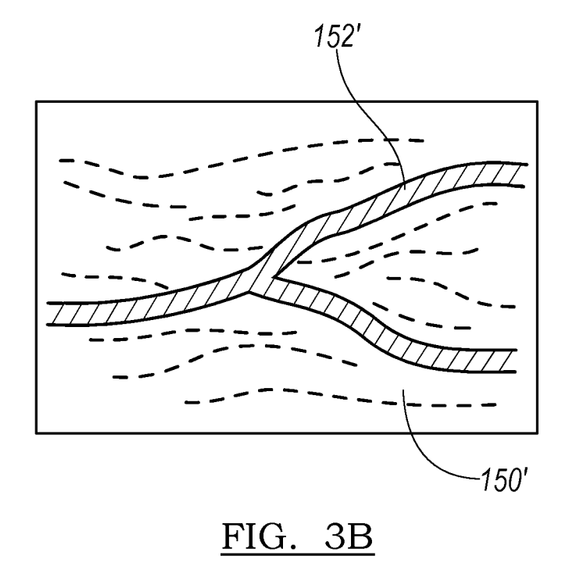
FIG. 3B is a schematic representation of a contrast enhanced image data.

With reference to FIG. 3A, image data acquired when powering the x-ray tube 100 with the power source 104 is schematically illustrated. As illustrated in FIG. 3A, the image data can include image data of soft tissue, such as surrounding tissues 150 that surround a vasculature 152. As illustrated in FIG. 3A, the power source A 104 can generate x-rays of the x-ray tube 100 that provide substantially little contrast between the vasculature 152 and the surrounding tissue 150, even if a contrast agent is present in the vasculature agent 152, such as iodine. With reference to FIG. 3B, however, the second power source B 106 can be used to generated second energy x-rays to acquire image data that illustrates the surrounding tissue 150' relative to the vasculature 152'. This can be further enhanced with a contrast agent that can be injected into the patient 14. As is understood in the art, the two power levels have different attenuations based on the materials in the patient 14. This differing attenuation can be used to differentiate materials, e.g. vasculature 152 and the surrounding tissue 150, in the patient 14.

With the acquisition of the image data illustrated in FIG. 3A and FIG. 3B, a reconstruction can be made to clearly identify the vasculature 152 of the patient 14 separate from the surrounding tissue 150 of the patient 14. The dual energy system can be used to reconstruct a model of the vasculature 152 of the patient 14 to discriminate the vasculature 152 from the surrounding tissue 150 of the patient 14. In identifying the vasculature 152, the imaging system 16, including the O-Arm® imaging system, can be used to efficiently image the vasculature 152 of the patient 14 in the operating theatre 10 during a procedure, such as a valve replacement procedure, a stent procedure, an inclusion ablation procedure, or an angioplasty procedure.

At least because the x-ray tube 100 is in a moveable imaging system, such as the imaging system 16, it can be moved relative to the patient 14. Thus, the x-ray tube 100 may move relative to the patient 14 while the energy for the x-ray tube 100 is being switched between the first power source 104 and the second power source 106. Accordingly, an image acquired with the first power source 104 may not be at the same pose or position relative to the patient 14 as the second power source 106. If a model is desired or selected to be formed of a single location in the patient 14, however, various interpolation techniques can be used to generate the model based on the amount of movement of the x-ray tube 100 between when the projection with the first power source 104 and the projection with the second power source 106 was acquired.

The dual energy of the x-rays emitted by the x-ray tube 100 due to the two power sources 104, 106 can allow for substantially efficient and enhanced contrast discrimination determination between the vasculature 152 and the musculature 150 of the patient 14. Moreover, the switching by a switch 102 between the power source A 104 and the power source B 106 allows for an efficient construction of the source 36 where the single x-ray tube 100 can allow for the generation of x-rays at two different energies to allow for enhanced or dynamic contrast modeling of the patient 14, such as modeling the vasculature of the patient 14 including a contrast agent therein.

The patient 14 can also be imaged with the injected contrast agent by gating the acquisition of the image data of the patient 14 based upon the injection of the contrast agent. According to various embodiments, a contrast agent, such as iodine, can be injected into the patient 14 to provide additional contrast in the image data acquired of the patient 14 with the imaging system 16. During the image acquisition, however, the contrast agent flows through the vasculature of the patient 14 from an artery phase to a venous phase. For example, the contrast agent can be injected into the patient 14 into an artery where the contrast agent can flow through the vasculature of the patient 14 to the heart, through the heart, to the lungs through the venous system, back through the heart, and out into the arterial portion of the vasculature of the patient 14.

When acquiring image data of the patient 14 to identify or reconstruct the vasculature of the patient 14, knowing the timing of when image data is acquired relative to the timing of the injection of the contrast agent can allow for a reconstruction of the various phases based on the known movement of the contrast agent through structures of the patient 14. In other words, it is generally understood that the contrast agent will flow through the patient 14 as described above at a known or generally known rate. As illustrated in FIG. 3B, the dual energy x-rays, generated with the x-ray tube 100 based upon the power source A 104 and the power source B 106, can be used to generate image data of any portion of the vasculature of the patient 14.

The acquisition of the image data, therefore, can be gated relative to the injection of the contrast agent into the patient 14. For example, the controls 32 of the imaging system 16 can be associated or communicate with a control of a pump 170 (illustrated in FIG. 1) through a communication line 172 (illustrated in FIG. 1) that pumps or injects the contrast agent into the patient 14. The communication 172 between the pump 170 and the imaging device control 32 can be any appropriate communication such as a wired, wireless, or other data communication system. Also, the control 170 for the pump can be incorporated into the controls 32 of the imaging system 16 or the processor system 26.

According to various embodiments, the control system 32 for the imaging system 16 can control the pump 170 to initiate injection of the contrast agent into the patient 14. The imaging system 16 can then acquire image data of the patient 14 over a set period of time to identify the difference between an arterial phase and a venous phase in the patient 14. For example, the imaging system can control the pump 170 to inject the contrast agent and then acquire image data for approximately 10 seconds to approximately 20 second including approximately 13 seconds. The imaging system 16 can identify or separate a first portion of the image data, such as about 5 second to about 7 seconds, including about 6 seconds as an arterial phase and a second phase of the image data, such as image data acquired after about 6 second to about 8 seconds, including about 7 seconds as a venous phase. In other words, the control system 32, or other appropriate processor system, can index the image data to determine when the image data was acquired. Also, it will be understood that the image data can be acquired at the two energies. Thus, the controls 32 or other appropriate processing system (e.g. a timer) can index the image data based on which of the two power sources 104, 106 were used to power the x-ray tube 100.

After the acquisition of the image data and determining a segregation of time of image data acquisition, a reconstruction of the vasculature of the patient 14 can then be made to illustrate or identify or reconstruct an arterial phase of the patient 14 and separately a venous phase of the patient 14. Accordingly, the imaging system 16 controlled with the controller 32 can be used to acquire image data of both a venous phase and an arterial phase of the patient 14 in a single image data acquisition sweep or period. In other words, the phase determination and reconstruction of an arterial phase and a venous phase of the vasculature of the patient 14 can be based on a single image data acquisition phase of the patient 14. Again, this can minimize or limit the exposure of the patient 14 and operating room staff to x-rays emitted from the x-ray tube 100 by requiring only a single image data acquisition phase. It will be understood, however, that a plurality of image data acquisition phases can be acquired of the patient 14.

The control system 32 of the imaging system 16 can be used to gate acquisition of the image data in addition to or with timing of the pump 170. For example, it can be selected to acquire image data of the vasculature of the patient 14 during diastole of the heart. During diastole of the heart of the patient 14, the heart generally does not move and blood in the vasculature is also relatively still. Accordingly, the image data can be acquired of the patient 14 by gating the acquisition of the image data relative to the heart movement of the patient 14. The generation of the x-rays with the x-ray tube 100 can be switched with the switch 102 to allow for time emission of x-rays from the x-ray tube 100.

The image data can be acquired by emitting x-rays from the x-ray tube 100 substantially sequentially such that at a selected period of time no x-rays are emitted by the x-ray tube 100 and at a different or second selected time x-rays are emitted from the x-ray tube 100. The x-rays emitted from one period to another can be at either of the two energies allowed by the power source A 104 or the power source B 106. Accordingly, at various times no x-rays can be emitted from the x-ray tube 100, but at other times x-rays can be emitted from the x-ray tube at a selected energy.

In being able to control the image system to emit or not emit x-rays image data acquisition can be gated relative to a physiological event of the patient 14. It will be further understood that gating of the image acquisition can be based upon respiration of the patient 14, physical movement of the patient 14, and other physiological events. The control system 32 can also be used to index the image data regarding whether acquired during a physiological event or not. The physiological event can be determined with an appropriate system, such as an electrocardiogram, or based on a regular rate of image acquisition (e.g. diastole occurs about 2 seconds in the patient 14).

Also, due to gating of the imaging system 16 relative to the patient 14, the control system 32 can also be used to control the imaging system 16 to control the speed of the detector 38 relative to the patient 14. As discussed above, the detector 38 of the imaging system can translate within the gantry 34 of the imaging system 16 to acquire image data of the patient 14. Further as discussed above, image data can be selected to be acquired of the patient 14 during only selected physiological events, such as diastole of the heart. To generate or form a three-dimensional model of at least a portion of the patient 14, it can be selected to have separation of a selected amount between acquisitions of images of the patient 14.

The detector 38 can be moved at a selected speed and change speeds to ensure appropriate separation of the images during the selected physiological events. The detector 38 can move at a first speed during a first physiological event such as systole of the heart, and at a second speed, such as a greater speed, during diastole of the heart to ensure appropriate separation of acquisition of images of the patient 14 during the selected physiological event.

In generating the 3D volumetric reconstruction to form the model, as discussed above, the model may be multi-phase to illustrate a selected portion of the patient to illustrate a first phase of physiological action and anatomical location and a second phase of physiological action and anatomical location. Thus, the model, or more than one model, can be used to illustrate a first phase (e.g. an arterial phase) and a second phase (e.g. venous phase) of the patient 14. Also, due to gating and movement of the detector 38 a first position of the detector 38 during image data acquisition and a second position of the detector 38 during image data acquisition can be used in the generating the first model and generating the second model to illustrate more than one phase of a physiological action of the patient 14. Additionally, the anatomy of the patient 14 and the physiology of the patient 14 can be used to form the 3D reconstruction. For example, the configuration of a bone of the patient 14 or a phase of a heart beat of the patient 14 can be used as a priori knowledge to assist in model reconstruction.

Also, the controller 32 of the imaging system 16 can be used to "rewind" or move the detector 38 back over the same path just traversed by the detector 38. Even while moving in a selected single path or direction, the detector 38 can be stopped and started, for example for gating or acquiring additional image data (e.g. x-ray projections) at a selected location. Accordingly, the controller 32 can control the imaging system 16 to achieve a selected separation of images relative to the patient 14 for reconstruction of an appropriate or selected model of the patient 14 based upon the required image data.

The reconstruction based on the image data or the raw image data can be used to perform a procedure on the patient 14. As discussed above selected navigation or tracking systems can be associated with the imaging system 16. Accordingly, the patient 14 can be registered to the image data and a navigation procedure can be performed. The navigated procedure can include placement of a stent in the patient's 14 heart, brain, or other vasculature, ablation procedures, angioplasty, implant placement or bone resection. Navigation can include tracking or determining automatically a location of an instrument positioned in a navigation field relative to a selected reference frame, such as in patient space, during a surgical procedure. The location of the instrument 66 can be illustrated on the display device 20 with an icon 174 that can be superimposed on the image data or the reconstructed model or image data 18.

In a subject, such as in the anatomy of the patient 14, various structures exist. Some structures can be imaged with various imaging modalities, for example x-ray imaging modalities, such as the O-Arm® imaging device 16. Some structures include the vasculature 152 of the patient 14. The vasculature 152 is generally not be imagable without the use of a contrast agent that is injected into the patient 14. The vasculature 152 also includes several phases or portions. As discussed in greater detail herein, the vasculature can include an arterial phase including arteries and a venous phase including veins. The two phases are distinguished by the purpose of the particular portion of the vasculature 152. In brief, the two phases can relate to one another regarding blood that has been oxygenated by traversing relative to the lungs in the arterial phase and the blood that is returning to the heart to be transferred to the lungs in the venous phase.

The contrast agent moves through the vasculature 152, due to flow of blood, and the imaging device 14 captures images over time as image frames as the contrast agent is moving. The contrast agent moves from one phase to another in sequence, as defined by the anatomy and physiology of the patient 14. Thus, the sequence of images includes images that relate only or substantially only to one phase in each image frame. In other words, if an image is taken when the contrast agent is in an artery then the image is from the arterial phase. Similarly, if an image is taken when the contrast agent is in a vein then the image is from the venous phase.

The acquired image data can be used to reconstruct a model, including a three-dimensional (3D) volumetric model of the various phases. The image data and/or reconstructed model can be used to plan or confirm a result of a procedure without requiring or using navigation and tracking. The image data can be acquired to assist in a procedure, such as an implant placement. Also, the image data can be used to identify blockages in the vasculature of the patient 14, such as with the contrast agent. Thus, navigation and tracking are not required to use the image data in a procedure. Also, the image data can relate to multiple different phases of the subject. The different phases can include an artificial phase (i.e. an arterial portion at the vasculature 152) or a venous phase (i.e. a venous portion at the vasculature 152).

Figure 4:
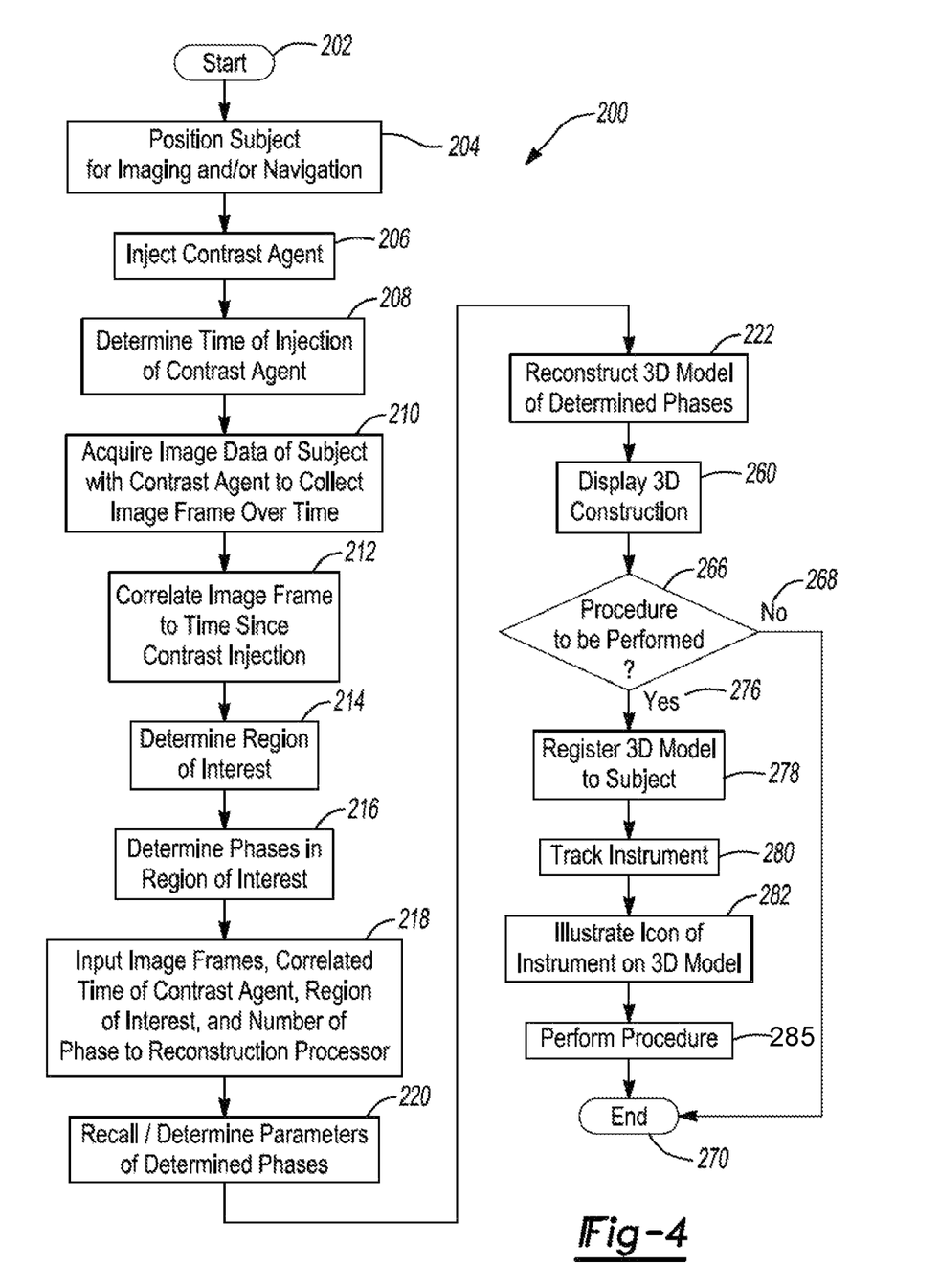
FIG. 4 is a flowchart of a method of reconstruction of a volume with acquired image data.

With reference to FIG. 4 a flowchart 200 illustrates a method of acquiring image data of a subject, such as the patient 14, to allow for reconstruction of multiple phases of various portions of the patient 14. As discussed herein, the vasculature 152 can include various phases and can be imaged particularly with a contrast agent. It will be understood, however, that other phases can also be determined based upon the region of the anatomy and the desire of viewing different portions or phases of the anatomy.

According to various embodiments, the imaging device 16 is operable to acquire image data of the patient 14 in a selected manner. For example, the image acquisition portion can move around the patient 14 generally in a circle or in various configurations of a helix, spiral, and other configurations relative to the patient 14. Due to the speed of material flowing through the vasculature 152 of the patient 14, however, the imaging system 16 may not be able to make an entire circle of the patient 14 while the contrast agent is in a single selected phase in the patient 14 (e.g. in an arterial phase, as discussed herein). Accordingly, it can be selected to determine in which phase a selected portion of the image data, such as a frame of image, is acquired of the patient 14.

According to the flowchart 200, particular phases of the patient 14 can be determined or reconstructed based upon acquired image data. Generally, the number of phases can be determined by a user, such as the user 12, and by the position of the contrast agent within the patient 14 over time. Image data acquired with the contrast agent allows for the acquisition of distinguishable or usable image data for forming a reconstruction of the patient 14, or a portion of the patient 14. For example, various soft tissue portions and vasculature may not generally be distinguishable using certain imaging modalities without a contrast agent. The reconstruction can be a volumetric or three-dimensional (3D) reconstruction or model of the patient 14. The 3D model can be used for various purposes, as discussed herein, such as to illustrate the position of the instruments (e.g. an ablation catheter) relative to the patient 14.

With continuing reference to FIG. 4 the flowchart 200 can begin at start block 202. A subject can be positioned for imaging in block 204. It is understood, that the subject 14 can be maintained in the same or generally same position for a navigated procedure as well. As illustrated in FIG. 1, the subject, which can include the patient 14, can be positioned relative to the imaging system 16. The patient 14 can be positioned on the table 15 and held in place with straps, or other holding systems. It is not required to fix the patient to the table 15 or provide any specific support of the patient 14. As discussed herein, the imaging system 16 can acquire image data of the patient 14. A selected image acquisition method can include acquiring a frame of image data at a selected point in space and at a selected point in time relative to the patient 14. The image frame can generally relate to a single instance of image acquisition and can form a portion of a collection of image data of the patient 14 where multiple image frames can be collected over time. In other words, the image frame can include a complete view by the image system 16 at one selected time and location.

Once the patient 14 has been positioned relative to the imaging system 16, in block 204, a contrast agent can be injected with the pump 170 in block 206. The contrast agent can be any appropriate contrast agent, including iodine or other contrast agents, which is operable to allow for a contrast between the vasculature 152 of the patient 14 and surrounding tissue 150 in the patient 14. Generally, soft tissue may not be substantially or adequately opaque when acquiring image data with x-rays. Thus, to acquire appropriate image data of the soft tissue or the vasculature 152 a contrast agent can allow for an appropriate opacity of the vasculature 152. The contrast agent can flow through the vasculature 152 being carried via the bloodstream. The opacity in the vasculature generates the appropriate contrast relative to the surrounding soft tissue for x-ray image acquisition. The pump 170 can be used to inject the contrast agent into the patient 14. The contrast agent then traverses the patient's vasculature 152 over time and, as such, moves through the various phases of the vasculature over time.

As discussed above, the pump 170 can be controlled relative to the imaging system 16, either directly with imaging system 16 or with the processor 28 to inject the contrast agent into the patient 14. The communication line 172 can be used to control the pump 170 for the injection of contrast agent. The time of the injection of the contrast agent can therefore be determined in block 208. The time of the injection of the contrast agent can be a selected absolute time (e.g. a particular hour, minute, and second) or can be a time relative to the acquisition of image data. For example, image data can be collected of the subject with a contrast agent injected in block 210. Accordingly the determination of time of injection in block 208 can correspond to the initiation of the image acquisition of the patient in block 210. In other words, the start of the injection of the contrast agent could be at time $T_0$ which could relate to a first image frame acquired with the imaging system 16. The initiation of the injection of the contrast agent could also be at time $T_0$. Time could then progress forward in selected steps (such as one second, two seconds, etc.) for image data acquisition and time from the initiation of the contrast agent injection. Therefore, the determination of time of injection of the contrast agent in block 208 can be either a relative time (e.g. relative to the acquisition of image data) or absolute time. Additionally, the time of acquisition of image data can also be determined.

As will be discussed in detail below, the contrast agent is injected into the patient 14 to allow for appropriate contrast that allows imaging of the vasculature of the patient 14. As discussed above, and illustrated in FIG. 3A, the vasculature 152 may generally be relatively indistinguishable relative to the soft tissue 150 surrounding the vasculature 152 using various imaging modalities, such as x-ray imaging. However, acquiring x-ray images in the operating theater 10 can be selected based upon costs, efficiency of image data acquisition, user selection, or the like. It can be selected, however, to attempt to minimize contrast agent injection into the patient 14 by acquiring substantially all necessary image data during one injection and image data acquisition cycle.

Figures 5A, 5B, 5C:
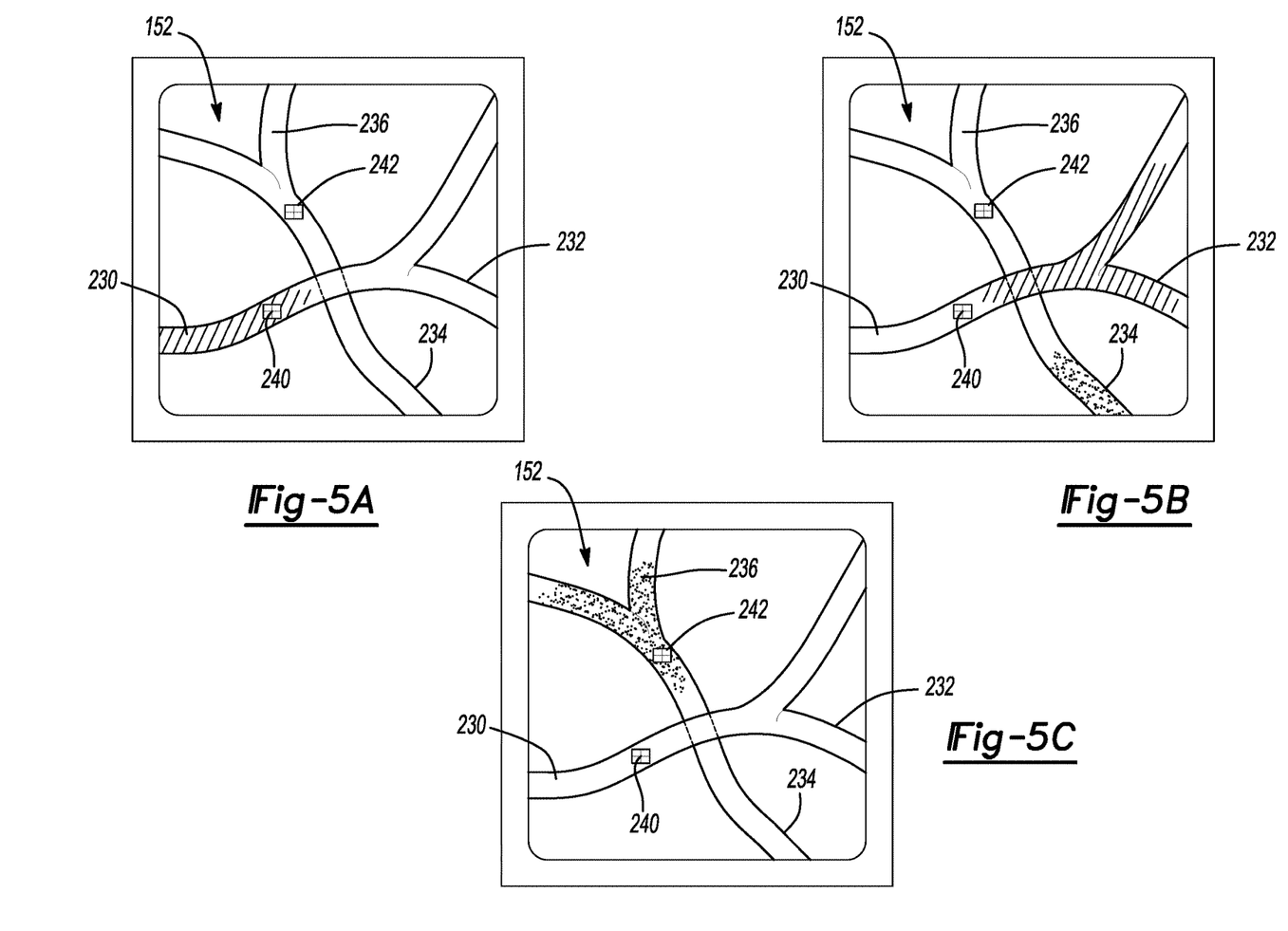
FIG. 5A-5C illustrate images and a contrast agent flowing through a portion of a subject.

As illustrated in FIGS. 5A-5C, however, the contrast agent generally washes or passes through different phases of the vasculature, such as an arterial phase and a venous phase, and collecting an appropriate amount of image data of the selected phases may be difficult. For example, a 360° collection of image data of a particular phase can be used to generate a three-dimensional reconstruction of the selected phase. If the imaging device 16 is unable to rotate fast enough relative to the patient 14, then a full 360° rotation of the patient 14 while the contrast agent is in a single phase, then one set of image data from a complete 360° rotation relative to the patient 14 will include multiple phases, as illustrated in FIGS. 5A-5C. Accordingly, the determination of input parameters including which frames belong to which phases, parameters regarding a peak and decrease of pixel intensity within the selected phases, and other parameters, including position of the imaging device 16 relative to the patient 14, can be used for an appropriate three-dimensional reconstruction.

As discussed above, the three-dimensional reconstruction can be based upon selected reconstruction algorithms. The reconstruction algorithms can include generating a model and reducing error between projections based on the acquired image data and an ideal model projection, as discussed above. Generally, the reconstruction uses the acquired two-dimensional image data to determine a theoretical projection based on the acquired images. Error is reduced between the theoretical projection and the model projection being made to reconstruct the reconstruction to a selected accuracy based on the acquired image data.

The image data, once collected or during collection, after injecting the contrast agent can be correlated in time to the injection or perfusion time of the contrast agent in the patient 14. A correlation can be made between the image frames and the time since injection as indicated in block 212. The correlation between the time since injection and the image frame can be based upon the determination of the time of injection in block 208 and the determination of the beginning of the image acquisition in block 214. For example, images can be collected at various time intervals, such as about one second apart. The timeline of the image frames collected with the imaging of system 16, therefore, can be correlated with perfusion (e.g. the time since contrast agent injection) time as determined in the series of images. The correlation of each image frame to a time of perfusion can be used to determine the phase for which the image was collected, including image data with the contrast agent injected into the patient 14 in that phase. Accordingly, an image frame that is taken after 30 seconds or after about 30 frames can be determined along with each of the other frames in the series of collected image data. In other words, each frame can be correlated to a specific time or to a relative time regarding the injection of the contrast agent. A timer can be provided with the pump and the imaging device 16 to record times relating to imaging time and perfusion time.

A determination of a region of interest can be made in block 214. The determination of the region of interest can be made prior to acquisition of the image data or at any selected time. Regions of interest can include cranial regions, abdominal regions, cardiac regions, peripheral regions, or any other appropriate region of the patient 14. The region can generally relate to a portion of the subject, such as a portion of the patient 14, which can be imaged in order to acquire image data of a vasculature within the region of interest.

After the determination of the region of interest is made in block 214, a determination of phases in the region of interest can be made in block 216. Again, the determination of the phases of interest can be made either prior to, during, or after the acquisition of the image data. The phases can include determining a number and/or determining or identifying the position of the contrast agent within the vasculature 152 of the patient 14. For example, as discussed above, an arterial phase and a venous phase can be two phases of the vasculature. It will be understood, however, that other phases can also be determined such as both early and late arterial phases and both early and late venous phases. Accordingly, the determination of phases can be made to allow for reconstruction of selected phases, such as reconstruction of only an arterial and only a venous phase or the reconstruction of an early arterial and a late arterial phases. The selection of phases is also used to determine which phases to reconstruct and assists in later correlation of image frames for reconstruction.

The determination of the number of phases in the region of interest can be based upon the parameters of the imaging system 16, such as the speed of acquisition of image data and the positions of the imaging device 16 relative to the patient 14. Regarding the speed of the imaging device 16, if the injection of the contrast agent into the patient 14 is made and the imaging system 16 is only able to collect 10 frames per second then collecting enough image data to reconstruct a large number of phases may not be possible. If the imaging device 16, however, is operable to collect 30 or 40 frames per second, then it may be possible to reconstruct a greater number of phases.

Generally, to reconstruct a three-dimensional model with a selected degree of accuracy it can be selected to acquire image data including at least an arc of at least about 150 degrees (°) to about 230°, including about 180° to about 210°, and further including about 200° of a single phase. Accordingly, the speed of movement of the imaging device 16 relative to the patient 14 can also limit or be used to determine the number of phases to be imaged. For example, if the imaging device 16 is able to move to acquire image data in at least a 200° arc relative to the patient 14 while the contrast agent is within the arterial phase then an arterial phase can be reconstructed. However, if the imaging device 16 is able to move in a 360° arc during the arterial phase then at least two phases of the arterial phase can be made, such as an early and the late arterial phase.

The imaging system 16 or other processing systems such as the processor system 26 of the modeling system, can be used to generate the reconstruction, as discussed above. In block 218 the image frames, the correlated time of contrast injection of agent in the frames, the region of interest and the number of phases of reconstruction can be input into the selected processor. Essentially, the frames of image data can be provided to the appropriate processor system along with a related time relative to the injection of the contrast agent and other parameters or constraints (including the region to be reconstructed and the phases in the region to be reconstructed). The parameters or constraints of the determined phases may also be recalled from a memory system and can be input in block 220.

Parameters or constraints can include time constraints regarding when a particular phase will have the contrast agent present for imaging. For example, the arterial phase can be constrained to the image frames between a first time point and a second time point. Accordingly, the correlated image frames can be broken into the particular time frames that would relate to be selected phases. Additionally timing of the contrast can be used to determine when the contrast may have moved from one phase to another phase in the image data. The number of phases can also be a constraint and used to determine which frames belong to which phase. Additionally, the perfusion or wash of the contrast agent through the selected regions, as illustrated by the selected phase pixels 240, 242 can be used to determine which pixels have an intensity relating to a presence of the contrast agent. The perfusion is based on the flow of material (e.g. blood) through the vasculature that is carrying the contrast agent.

The input of the determined parameters can be input by the user 12 during the procedure, such as with the input device 24, or can be recalled from a selected memory system based upon the determined region of interest and phases of interest. The parameters, as discussed herein, can be used to allow for the reconstruction of a three-dimensional volume based upon the plurality of image frames collected of the patient 14 during the image acquisition phase.

The model can be reconstructed in block 222 based upon the image data acquired at the patient 14 and the input parameters from block 220. As exemplary illustrated in FIGS. 5A-5C, frames of image data can be collected of the patient 14. As discussed above, the vasculature 152 of the patient 14 can include various phases which denote different physical anatomical locations within the patient 14. Exemplary phases can include an early arterial phase 230 and a late arterial phase 232, early venous phase 234 and the late venous phase 236. As discussed above, the early and late portions of the different phases may not be distinguishable with the image data, but are illustrated here for the following discussion as an example of various parameters that can be input into the system. The imaging device 16 would need to acquire the image data at an appropriate rate to be able to determine or reconstruct both an early and late phase of a particular phase, such as an arterial and venous phase.

As illustrated in FIG. 5A, an arterial pixel or region 240 can be selected or determined that is within the arterial phase and a venous pixel or region 242 can be chosen that is within the venous phase. As illustrated by the cross-hatching in FIG. 5A, the contrast agent is within the early arterial phase 230 and FIG. 5A illustrates image data able to be captured due to the presence of the contrast agent in the vasculature 152. In FIG. 5B the contrast agent has passed into the late arterial phase 232, as shown by the cross-hatching in the late arterial phase region 232. Also, as illustrated in FIG. 5B, the contrast agent is illustrated as it begins to move into the early arterial phase 234, illustrated by the dotted region in the early venous phase 234.

The arterial pixel 240 in the arterial phase can be input as a parameter that is expected to have a peak of contrast (or a peak image intensity or darkness) at a certain time after the injection of the contrast agent. Accordingly, the image frames that include high contrast in the selected region at the parameter time for the arterial phase can be included for the reconstruction of the arterial phase. In other words, the arterial pixel 240 will have high contrast during the arterial phase. Thus, any pixel in the image data with high contrast during the selected time or selected image frames of the arterial phase will be used in the reconstruction of the arterial phase. It will be understood, that the arterial region 240 in the arterial phase can be a single pixel or group of pixels selected either prior to the reconstruction determination or during the reconstruction determination that meets the contrast or position parameter. Various parameters can also include the speed of wash or change in intensity of the selected region, such as at the arterial pixel 240, which is known based upon speed of movement of the contrast agent through the vasculature 152 of the patient 14. Thus, the change in the arterial pixel intensity can be used to confirm that a pixel, such as the arterial pixel 240, is an arterial phase pixel that should be selected for performing the reconstruction in block 222 of the arterial particular phase.

Another input parameter can include constraining which image frames relate to selected phases. For example, that image frames 5 through 95 of a series of image frames, based upon a speed of the image data acquisition and speed of movement of the imaging device 16, can include the arterial phase. If a pixel shows a high contrast during these frames, particularly when compared to other frames, that pixel (e.g. the arterial pixel 240) can be determined to be in the arterial phase. Accordingly, the time of injection of the contrast agent and the time of the frames collected after the injection of the contrast agent can be used for the determination of the phase that is imaged in the selected frame and this determination is used for determining which phase should be reconstructed with image data from that frame.

Similarly, the venous phase pixel 242 can have similar wash or selected wash parameters to determine that the venous pixel 242 is within the venous phase. The wash parameters of selected frames can be based on the speed of movement of the contrast agent with the patient 14. For example, it can be determined that image frames 110 through 220, of a series of frames, of the acquired image data can be those that relate to the venous phase based upon the speed of wash of the contrast agent through the vasculature 152 of the patient 14. The change in intensity of the venous pixel 242 within the image data over time can be used to identify a venous phase. As illustrated in FIG. 5C, by the dotted portion in the late venous phase 236, the contrast agent is washing through or past the venous pixel 242. The timing associated with the image frame illustrated in FIG. 5C can be used to determine that the contrast agent (and thus image data due to the presence of the contrast agent) is within the venous phase or some portion of the venous phase.

Figures 6A, 6B, 7:
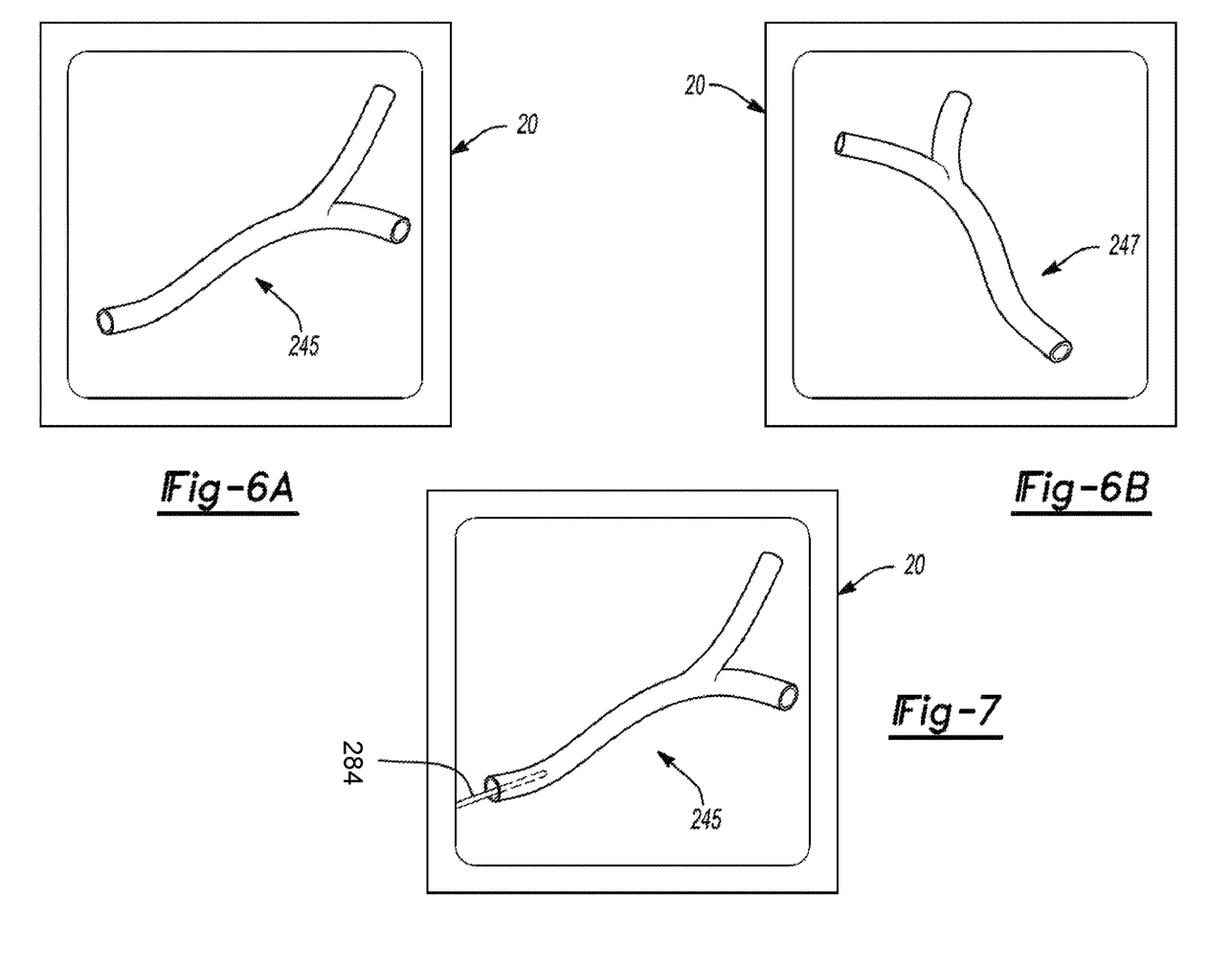
FIGS. 6A and 6B illustrate reconstructions of two different phases of the subject.
FIG. 7 illustrates a view of an instrument icon superimposed on a reconstruction of one of the phases from FIGS. 6A and 6B.

Once the image data is collected with the contrast agent injected, the image data is correlated, as discussed above, and a reconstruction of the vasculature can occur. Regardless of the reconstruction method used, a display of selected vasculature phases can be made on the display device 20 as illustrated in FIGS. 6A and 6B. The reconstruction can be a volumetric or three-dimensional reconstruction. Due to the determination of specific phases and the parameters discussed above, the reconstruction algorithm can be used to reconstruct separate and distinct phases of the anatomy. For example, the early and late arterial phase 230, 234 can be illustrated together as a single arterial phase 245 based upon the parameters discussed above, including the limitations of the imaging device 16. The arterial phase model 245 can include a volumetric display of the entire arterial phase within the region of interest selected in block 214. Additionally, as illustrated in FIG. 6B, a venous phase model can include both the early and late venous phases 234, 236 and can be illustrated as a single venous phase model 247. Again, the number of phases can be selected by the user 12 or be based upon limitations of the imaging device 16. Nevertheless, the display device 20 can display either or both of the phases or any of the phases selected for the region of interest.

Once the reconstruction of the models is made in block 222, it can be displayed in block 260, and a determination of whether a procedure is to be performed can be made in block 266. If no procedure is to be performed, then the NO path 268 can be followed to the end block 270. When no procedure is to be performed the image data, including the reconstructed models from block 222, can be used for analysis of the patient 14. For example, the structure of the vasculature can be determined based upon the three-dimensional models including any blockages, embolisms, or the like.

If it is determined that a procedure is to be performed in block 266, then a YES path 276 can be followed to register the three-dimensional model to the subject in block 278. The registration of the model to the subject in block 278 can be based upon the registration techniques discussed above. For example, the image data is acquired with the imaging system 16 and the position of the imaging device 16 relative to the patient 14 can be known based upon the movement of the imaging device 16 relative to the patient 14 and/or tracking the imaging device 16 and the patient 14. The known position of the imaging device 16 relative to the patient 14 can be used to register the models that are generated with the image data frames acquired of the patient at the known locations. Additionally, reference devices or fiducials can be positioned in the patient 14 to determine registration of known locations relative to the generated models.

Once the image data and the models are registered, an instrument can be tracked in block 280. The instrument can be any appropriate instrument, such as an ablation catheter or other selected instrument. An icon 284 can be displayed on the display device 22 to represent the location of the instrument relative to the model, as illustrated in FIG. 7 in block 282. The icon 284 can illustrate the location of the tracked instrument relative to the reconstruction of the selected phase, such as, for example, the arterial phase 230, 232. Accordingly, tracking the instrument within the patient 14 can be made and displayed on the display device to allow the user 12 to determine a location of the instrument relative to the vasculature 152 of the patient 14. A procedure can be performed in block 285 and the method can then end in block 270. The procedure can be any appropriate procedure such as an ablation near a heart, a stent placement, an embolism repair, etc.

Accordingly, a reconstruction of various phases of the vasculature 152 of the patient 14 can be made based upon the selected parameters of the image data acquisition and contrast agent within the patient 14, as discussed above. This can allow for reconstruction of portions of the patient 14 that are generally indistinguishable or not easily distinguished based on various imaging modalities. This can allow for reconstruction of models, including three-dimensional volumetric models, based upon acquired serial image frames of the patient 14. The parameters of the perfusion of the contrast agent within the patient 14 and properties of the imaging device 16 can be used for determination and selection of frames of the image data and portions of the phases that can be reconstructed. Thus, even if a single phase can not be imaged by an entire 360 degree rotation of an imaging device relative to the patient 14, a single phase can still be reconstructed using the parameters and constraints discussed above. The reconstruction can be based upon parameters of time, movement of the contrast agent, and the like, and can be used to substantially volumetrically generate three-dimensional reconstructions based upon the limited acquired image data.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method reconstructing multiple phases of a vasculature of a subject, comprising:
    operating a x-ray source at a first power to emit x-rays to be detected by a detector at a selected imaging first time;
    operating the x-ray source at a second power to emit x-rays to be detected by the detector at the selected imaging second time, wherein the second power is selected to have a voltage that is about 40 kV to about 60 kV different than the first power and an amperage that is about 20 mA to about 150 mA different than the first power;
    moving the x-ray source and the detector along a selected path relative to the subject; and
    acquiring image data of a selected portion of the subject over an imaging period of time while (i) moving the x-ray source and the detector and (ii) switching between powering the x-ray source at the first power to emit x-rays to be detected by the detector and powering the x-ray source at the second power to emit x-rays to be detected by the detector, wherein the acquired image data includes a plurality of image frames of the subject acquired over the imaging period of time at both (i) different positions relative to the subject based on the moving of the x-ray source and the detector and (ii) different powers operable to assist in discriminating the vasculature of the subject from a tissue surrounding the vasculature of the subject based on a difference in the image data due to the difference of the first power and the second power;
    receiving via an input directly from a user an identification in a region of interest regarding the vasculature of the subject of at least a phase image portion regarding a first phase and a second phase, wherein the phase image portion is operable to determine which one or more portions of the image data have an intensity relating to a presence of a contrast agent;
    determining a first sub-plurality of image frames of the plurality of image frames of the acquired image data that relate to the first phase of the vasculature of the subject in the region of interest based at least on the received input;
    determining a second sub-plurality of image frames of the plurality of image frames of the acquired image data that relate to the second phase of the vasculature of the subject in the region of interest based at least on the received input;
    reconstructing a model that illustrates both (i) at least one of the first phase of the vasculature of the subject based on the determined first sub-plurality of image frames or the second phase of the vasculature of the subject based on the determined second sub-plurality of image frames and (ii) the discrimination of the first phase of the vasculature of the subject or the second phase of the vasculature of the subject from the tissue surrounding the vasculature of the subject, wherein at least one of the first phase or the second phase is reconstructed using the input and wherein the model is constructed based on the acquired image data;
    registering the reconstructed model to the subject such that a location in a navigation field is operable to be displayed on a display device relative to the reconstructed model; and
    generating for display on the display device a graphical representation of an instrument superimposed on a display of the reconstructed model, wherein the instrument is tracked relative to the subject and the generated graphical representation that is displayed is based on the tracked instrument and the registration of the reconstructed model to the subject.

2. The method of claim 1, wherein reconstructing a model that illustrates at least one of the first phase of the subject based on the determined first sub-plurality of image frames or the second phase of the subject based on the determined second sub-plurality of image frames includes reconstructing a dual model to illustrate both the first phase and the second phase;
    wherein the received input includes at least a time constraint or the phase image portion in the plurality of image frames.

3. The method of claim 2, further comprising:
operating a display device to display the dual phase model.

4. The method of claim 2, further comprising:
executing instructions with a processor to determine the model that illustrates at least one of the first phase of the subject based on the determined first sub-plurality of image frames or the second phase of the subject based on the determined second sub-plurality of image frames.

5. The method of claim 4, wherein executing instructions with the processor to determine the model includes constructing a multi-phase model to illustrate a venous phase of the vasculature of the subject and an arterial phase of the vasculature of the subject.

6. The method of claim 1, further comprising:
injecting the contrast agent into the vasculature of the subject at a selected injection start time;
correlating the plurality of image frames over time to a position of the contrast agent in the region of interest within the subject over time;
wherein the received input relates to the image portion intensity in the region of interest.

7. The method of claim 6, wherein determining the first sub-plurality of image frames of the plurality of image frames that relate to the first phase in the subject is based on the correlating the plurality of image frames over time to the position of the contrast agent in the subject over time;
wherein moving the x-ray source and the detector along a selected path relative to the subject comprises controlling with a controller of an imaging system a selected path including selected movements of at least one of the x-ray source, the detector, and a gantry, wherein the gantry encloses the x-ray source and the detector.

8. The method of claim 7, wherein determining the second sub-plurality of image frames of the plurality of image frames that relate to the second phase in the subject is also based on the correlating the plurality of image frames over time to the position of the contrast agent in the subject over time.

9. A method reconstructing multiple phases of a vasculature of a subject, comprising:
injecting a contrast agent into the vasculature of the subject at a selected injection start time, wherein the contrast agent injected into the subject has a x-ray scattering pattern different than that of an anatomy of the subject;
powering a x-ray source tube to emit x-rays at a first power with a first power source to acquire a first image data at a first position along a path relative to the subject and having a first attenuation within the subject;
powering the x-ray source tube to emit x-rays at a second power different from the first power with a second power source to acquire a second image data at a second position along the path relative to the subject and having a second attenuation within the subject;
providing an imaging system having a cart, a gantry moveable relative to the cart, the x-ray source tube within the gantry, wherein the gantry encloses the x-ray source and is provided to encircle the subject;
acquiring the first image data and the second image data of the vasculature of the subject at both the first power and the second power while at least one of positioning or moving the x-ray source within the gantry and at least one of moving or not moving the gantry;
determining a region of interest including the vasculature of the subject;
determining a first portion of the first image data that relates to the first phase of the vasculature of the subject in the determined region of interest based at least on a received input directly from a user and a second portion the second image data that relates to the second phase of the vasculature of the subject in the determined region of interest based at least on the received input; and
reconstructing a model of the vasculature of the subject in the determined region of interest based on an iterative process using the first image data with the first attenuation and the second image data with the second attenuation based on the first power and the second power;
wherein reconstructing the model includes:
constructing a multi-phase model that illustrates all of (i) a first phase of the vasculature of the subject including a venous phase of the subject in the first image data and the second image data, (ii) a second phase of the vasculature of the subject including an arterial phase of the subject in the first image data and the second image data, and (iii) a discrimination of the first phase or the second phase from tissue surrounding the vasculature of the subject.

10. The method of claim 9, wherein the iterative process includes iteratively changing a pre-formed theoretical image data projection of the subject until the pre-formed theoretical image data projection matches the acquired image data of the subject to form an appropriately altered reconstruction model.

11. The method of claim 9, further comprising:
selecting the first power to have a first voltage of about 40 kV to about 180 kV and a first amperage of about 10 mA to about 500 mA;
selecting the second power to have a second voltage that is about 40 kV to about 60 kV different than the first voltage and a second amperage that is about 20 mA to about 150 mA different than the first amperage.

12. The method of claim 11, further comprising:
moving the x-ray source tube along the path relative to the subject within the gantry and by movement of the gantry that encloses the x-ray source tube;
moving a detector within the gantry to detect x-rays emitted by the x-ray source; and
controlling the moving of the x-ray source tube, the gantry, and the detector with a controller;
wherein the x-ray source tube is a single x-ray source tube powered by both the first power source and the second power source.

13. The method of claim 12, wherein reconstructing the model further includes:
executing instructions with a processor to determine a difference between the first image data acquired at the first power and the second image data acquired at the second power;
wherein the discrimination of the first phase or the second phase from tissue surrounding the vasculature of the subject includes differentiating the vasculature from the surrounding tissue based on the first image data acquired at the first power and the second image data acquired at the second power;
wherein reconstructing the model includes executing instructions with the processor to reconstruct a model of the selected portion of the subject including illustrating a first region in the selected portion and a second region in the selected portion based on the determined difference in the first image data and second image data.

14. The method of claim 13, further comprising:
executing instructions with a processor to:
construct the multi-phase three-dimensional model of the selected portion of the subject operable to be displayed on a display device; and
generate for display on the display device a graphical representation of an instrument, wherein the instrument is tracked relative to the subject and the generated display of the graphical representation is based on the tracked instrument and a registration of the multi-phase three-dimensional model to the subject.

15. A system configured to reconstruct multiple phases of a vasculature of a subject, comprising:
a pump to inject a contrast agent into the vasculature of the subject at a selected injection start time, wherein the contrast agent injected into the subject has a x-ray scattering pattern different than that of an anatomy of the subject;
an imaging system including:
a x-ray source;
a detector to detect x-rays emitted by the x-ray source and generate an image data;
a gantry configured to enclose both the x-ray source and the detector and in which both the x-ray source and the detector are configured to move, wherein the gantry is further configured to encircle the subject;
a first power source to power the x-ray source at a first power to emit x-rays to be detected by the detector at a selected imaging first time; and
a second power source to power the x-ray source at a second power to emit x-rays to be detected by the detector at a selected imaging second time;
wherein the second power source has a voltage that is about 40 kV to about 60 kV different than the first power source and an amperage that is about 20 mA to about 150 mA different than the first power source;
a controller in communication with the imaging system and the pump operable to provide the imaging system instruction to the imaging system and the pump instruction to the pump to control initiation and timing of the injection of the contrast agent into the subject and to acquire the image data based upon the initiation and timing of the injection of the contrast agent and a path;
wherein the x-ray source and the detector are configured to move in a selected path relative to the subject based on the imaging system instruction; and
wherein the image data is of a selected portion of the subject over an imaging period of time and is acquired while (i) moving the x-ray source and the detector along the path and (ii) switching between powering the x-ray source at the first power to emit x-rays to be detected by the detector and powering the x-ray source at the second power to emit x-rays to be detected by the detector, wherein the image data includes a plurality of image frames of the subject acquired over the imaging period of time at both (i) different positions relative to the subject based on the moving of the x-ray source and the detector and (ii) different powers; and
an image data indexer configured to (i) receive inputs from a user regarding parameters of a first anatomical phase and a second anatomical phase from the user related to a region of interest of the subject and (ii) index the plurality of image frames of the subject based at least on a time stamp by the controller and execute instructions to determine whether a selected portion of the image data is regarding the first anatomical phase or the second anatomical phase based on at least the plurality of image frames of the subject and the received inputs;
wherein the image data indexer comprises a processor system configured to, based on the region of interest, determine a first sub-plurality of image frames of the plurality of image frames that relate to the first anatomical phase and a second sub-plurality of image frames of the plurality of image frames that relate to the second anatomical phase.

16. The system of claim 15, wherein the processor system is further configured to differentiate the first anatomical phase and the second anatomical phase from a surrounding tissue based on the emitted x-rays at the first power and the emitted x-rays at the second power and different attenuations of the x-rays at the first power and the x-rays at the second power between the surrounding tissue and either of the first anatomical phase and the second anatomical phase.

17. The system of claim 16, wherein the processor system is further configured to reconstruct a model that illustrates at least one of the first anatomical phase based on the determined first sub-plurality of image frames or the second anatomical phase based on the determined second sub-plurality of image frames.

18. The system of claim 17, wherein the processor system is further configured to reconstruct the model to illustrate both the first anatomical phase based on the determined first sub-plurality of image frames and the second anatomical phase based on the determined second sub-plurality of image frames;
wherein the received inputs an identification of a phase pixel in the region of interest to identify the first sub-plurality of image frames relating to the first anatomical phase and the second sub-plurality of image frames relating to the second anatomical phase;
wherein the phase image pixel is operable to determine which one or more portions of the image data have an intensity relating to a presence of the contrast agent.

19. The system of claim 18, further comprising:
a display device configured to display the model to illustrate both the first anatomical phase based on the determined first sub-plurality of image frames and the second anatomical phase based on the determined second sub-plurality of image frames.

20. The system of claim 19, further comprising:
a navigation system having a tracking system and an instrument tracking device and a gantry tracking device;
wherein the navigation system is configured to:
register the model to the subject based at least in part on tracking the gantry with the gantry tracking device;
determine a tracked location of the tracking device; and
determine a location of an icon to be superimposed on the displayed model representing a location of an instrument relative to the determined tracked location of the tracking device relative to the subject;
wherein the model is a three-dimensional model.

* * * * *

UNITED STATES PATENT AND TRADEMARK OFFICE
CERTIFICATE OF CORRECTION

PATENT NO. : 11,969,279 B2
APPLICATION NO. : 15/823031
DATED : April 30, 2024
INVENTOR(S) : Patrick A. Helm et al.

Page 1 of 1

It is certified that error appears in the above-identified patent and that said Letters Patent is hereby corrected as shown below:

On the Title Page

Page 3, Column 1, item (56) Other Publications, Line 33, Delete "3." and insert --3,-- therefor Page 3, Column 1, item (56) Other Publications, Lines 34-35, Delete "12/908,189, filed Oct. 20, 2010" and insert --13/016,718, filed Jan. 28, 2011-- therefor Page 3, Column 2, item (56) Other Publications, Line 42, Delete "realted" and insert --related-- therefor In the Specification Column 10, Detailed Description, Line 26, Delete "14" and insert --16-- therefor Column 15, Detailed Description, Line 12, Delete "234," and insert --230,-- therefor Column 16, Detailed Description, Line 14, Delete "234" and insert --232-- therefor Column 16, Detailed Description, Line 59, Delete "22" and insert --20-- therefor In the Claims Column 21, Line 51, In Claim 15, after "inputs", insert --directly--

Signed and Sealed this
Eighteenth Day of March, 2025

Coke Morgan Stewart
*Acting Director of the United States Patent and Trademark Office*